US009677924B2

(12) United States Patent
Maguin

(10) Patent No.: US 9,677,924 B2
(45) Date of Patent: Jun. 13, 2017

(54) METHOD FOR MEASURING ULTRASONICALLY THE FILL LEVEL OF A LIQUID

(71) Applicant: CONTINENTAL AUTOMOTIVE GMBH, Hannover (DE)

(72) Inventor: Georges Maguin, Marly (FR)

(73) Assignee: Continental Automotive GmbH, Hannover (DE)

( * ) Notice: Subject to any disclaimer, the term of this patent is extended or adjusted under 35 U.S.C. 154(b) by 57 days.

(21) Appl. No.: 14/652,179

(22) PCT Filed: Dec. 11, 2013

(86) PCT No.: PCT/EP2013/076169
§ 371 (c)(1),
(2) Date: Jun. 15, 2015

(87) PCT Pub. No.: WO2014/090848
PCT Pub. Date: Jun. 19, 2014

(65) Prior Publication Data
US 2015/0323373 A1 Nov. 12, 2015

(30) Foreign Application Priority Data
Dec. 14, 2012 (EP) .................................. 12290441

(51) Int. Cl.
*G01F 23/296* (2006.01)
*G01N 29/024* (2006.01)
*F01N 3/20* (2006.01)

(52) U.S. Cl.
CPC ....... *G01F 23/2962* (2013.01); *F01N 3/2066* (2013.01); *G01N 29/024* (2013.01);
(Continued)

(58) Field of Classification Search
CPC . G01N 29/024; F01N 3/2066; G01F 23/2962; G01F 23/296; G01F 23/2968
See application file for complete search history.

(56) References Cited

U.S. PATENT DOCUMENTS 5,095,748 A * 3/1992 Gregory .............. G01F 23/2961
702/54
5,793,705 A * 8/1998 Gazis .................... G01F 23/296
367/98

(Continued)

FOREIGN PATENT DOCUMENTS

DE 10 2010 035 008 A1 2/2012

*Primary Examiner* — Paul West
*Assistant Examiner* — Xin Zhong
(74) *Attorney, Agent, or Firm* — Laurence A. Greenberg; Werner H. Stemer; Ralph E. Locher

(57) ABSTRACT

A method for measuring the fill level of a liquid additive in a tank using an ultrasonic sensor includes initially carrying out a measurement of a first propagation time of an ultrasonic signal from the ultrasonic sensor to a liquid level of the liquid additive. This is followed by cleaning of at least one reference surface in the liquid additive with the aid of at least one ultrasonic pulse. Then at least one second propagation time of an ultrasonic signal from the ultrasonic sensor to the at least one reference surface is measured and the fill level is calculated from the first propagation time and the second propagation time. A delivery unit having at least one ultrasonic sensor for installation in a liquid additive tank is also provided.

11 Claims, 2 Drawing Sheets

(52) U.S. Cl.
CPC *F01N 2610/142* (2013.01); *F01N 2900/1814* (2013.01); *G01N 2291/0222* (2013.01); *G01N 2291/02809* (2013.01); *G01N 2291/02836* (2013.01); *Y02T 10/24* (2013.01)

(56) References Cited

U.S. PATENT DOCUMENTS

| | | | | |
|---|---|---|---|---|
| 5,856,953 | A * | 1/1999 | Durkee | G01F 23/2962 367/908 |
| 6,078,850 | A * | 6/2000 | Kane | G06Q 50/06 340/439 |
| 8,943,812 | B2 * | 2/2015 | Schepers | G01F 23/00 181/124 |
| 2004/0007061 | A1 * | 1/2004 | Forgue | G01F 23/2968 73/290 V |
| 2010/0257931 | A1 * | 10/2010 | Partington | G01F 23/2962 73/290 V |
| 2012/0118059 | A1 * | 5/2012 | Reimer | F01N 3/2066 73/290 V |

\* cited by examiner

METHOD FOR MEASURING ULTRASONICALLY THE FILL LEVEL OF A LIQUID

BACKGROUND OF THE INVENTION

Field of the Invention

The invention relates to a method for measuring the fill level of a liquid additive in a tank. The liquid additive in the tank can, for example, be provided for use in a motor vehicle.

In the automotive field, for example, exhaust-gas purification devices are wide-spread, in which the exhaust gases of a combustion engine are purified with the aid of a liquid additive. By way of example, the method of selective catalytic reduction is known [SCR method; SCR=selective catalytic reduction], in which a reducing agent as liquid additive is added to the exhaust gas and nitrogen oxide compounds in the exhaust gas are reduced with the aid of the reducing agent. A urea/water solution is regularly used as reducing agent for the SCR method; it can be stored and provided as liquid additive and then converted to ammonia prior to the addition to the exhaust gas and/or in the exhaust gas. The actual reducing reaction then occurs between the ammonia and the nitrogen oxide compounds in the exhaust gas. The conversion of urea/water solution into ammonia occurs thermally in the exhaust gas as a result of the exhaust-gas heat and/or hydrolytically, i.e. supported by a hydrolysis catalyst. The conversion can occur in the exhaust gas or in an exhaust-gas-external convertor. A urea/water solution with a urea content of 32.5 percent is available under the trade name AdBlue as a liquid additive for the SCR method.

Fill-level sensors are typically provided on the tank in order to monitor the amount of available reducing agent in a tank in a motor vehicle. In this context, the use of ultrasonic sensors is also known; these can be used to determine the fill level with the aid of a propagation time measurement of an ultrasonic signal in the liquid additive. A propagation time is usually measured from an ultrasonic emitter at the bottom of the tank up to a liquid level in the tank and back to an ultrasonic receiver on the tank bottom. To this end, the ultrasonic signal emitted by the ultrasonic emitter is reflected at the liquid level. The distance of the liquid level can be determined from this propagation time on the basis of the propagation speed of the ultrasonic signal in the liquid additive.

The propagation speed of the ultrasonic waves in a tank regularly depends on the composition of the liquid additive. This composition may change as a result of variations in quality and concentration. Hence an additional reference measurement is typically carried out in the case of ultrasonic sensors. The propagation time of an ultrasonic signal from an ultrasonic sensor to a reference surface and back to the ultrasonic sensor is determined during this reference measurement. In this case, the length of the path from the ultrasonic sensor to the reference surface is known precisely. Moreover, this path is completely filled with liquid additive. Thus the path is situated below the liquid level in its entirety. The propagation time measurement of the ultrasonic signal along the path allows the propagation speed of the ultrasonic signal in the liquid additive to be determined precisely. The propagation speed of the ultrasonic signal established thus can be used to correct or calibrate the measurement of the distance between the liquid level and the ultrasonic sensor.

It was found, particularly in the case of a urea/water solution as a liquid additive, that impurities and/or gas collections on or at the reference surfaces are problematic for the ultrasonic measurement. Impurities on the reference surfaces can have a significant adverse effect on the measurement of the propagation time to the reference surface because the ultrasonic signal is reflected and scattered in uncontrolled fashion by the impurities at the reference surface. Hence it may be the case that a clear ultrasonic signal is no longer reflected at the reference surface and the propagation time can no longer be measured accurately.

BRIEF SUMMARY OF THE INVENTION

Proceeding therefrom, it is an object of the present invention to solve or at least mitigate the technical problems described in conjunction with the prior art. In particular, a particularly advantageous method for measuring the fill level of a liquid additive in a tank is to be presented.

These objects are achieved by a method having the steps recited below. Further advantageous embodiments of the method are specified in the claims which are worded as being dependent. The features listed individually in the claims can be combined as desired in a technologically expedient way and can be complemented by explanatory facts from the description, wherein further embodiment variants of the invention are highlighted.

A method for measuring the fill level of a liquid additive in a tank using an ultrasonic sensor, comprising at least the following steps:

a) measuring a first propagation time of an ultrasonic signal from the ultrasonic sensor to a liquid level of the liquid additive;

b) cleaning at least one reference surface in the liquid additive with the aid of at least one ultrasonic pulse;

c) measuring at least one second propagation time of an ultrasonic signal from the ultrasonic sensor to the at least one reference surface; and d) calculating the fill level from the first propagation time and the second propagation time, is in accordance with the invention.

The liquid additive is preferably the urea/water solution described further above. The tank is preferably provided for use in a motor vehicle, for storing the liquid additive and supplying it to an exhaust-gas treatment device. The ultrasonic sensor is preferably arranged in the region of the bottom of the tank and preferably comprises an ultrasonic transmission unit and an ultrasonic reception unit. The ultrasonic transmission unit is configured to emit ultrasonic signals. The ultrasonic reception unit is configured to receive reflected signals which go back to the emitted ultrasonic signal. The ultrasonic transmission unit and the ultrasonic reception unit are preferably integrated together in a (single) ultrasonic sensor. The ultrasonic transmission unit is preferably aligned such that it emits ultrasonic signals vertically against a liquid level in the tank from below. The liquid level in the tank corresponds to the liquid surface which arises in the tank in the case of a specific filling quantity of liquid additive in the tank as a result of gravity. The liquid level is the interface between the liquid additive and a gas (in particular air), which is present in the tank above the liquid additive.

When measuring the first propagation time in step a), the propagation time of an ultrasonic signal is determined along a straight line from the ultrasonic sensor to the liquid level and back to the ultrasonic sensor. To this end, the ultrasonic signal used for this is preferably emitted by an ultrasonic transmission unit and received by an ultrasonic reception unit.

An ultrasonic pulse rather than an ultrasonic signal is used during the cleaning of the reference surface in step b). An ultrasonic pulse does not differ per se from an ultrasonic signal. The difference merely lies in the fact that no ultrasonic reception unit expects a response signal in the case of an ultrasonic pulse. The ultrasonic pulse in step b) is preferably configured such that impurities on the reference surface can be removed or dissolved by the ultrasonic pulse. By way of example, at least one of the following parameters of the ultrasonic pulse can be selected suitably to this end (and can in this respect also differ from the ultrasonic signal used for the measurement):

the frequency of the ultrasonic pulse;
the duration of the ultrasonic pulse; and
the amplitude of the ultrasonic pulse.

In the liquid additive, the ultrasound propagates like a longitudinal wave. A longitudinal wave oscillates along the direction of propagation. The frequency and the amplitude of the ultrasonic pulse mean the frequency and the amplitude of this longitudinal wave. The amplitude can be specified either in the form of a maximum pressure occurring during the oscillation or in the form of a maximum movement and/or displacement of the liquid additive occurring during the oscillation. The duration of the ultrasonic pulse is preferably defined by the period of time from the start of the emission of the ultrasonic pulse until the end of the emission of the ultrasonic pulse.

By way of example, impurities on the reference surfaces can be gaseous bubbles and/or solid deposits. Gaseous bubbles can comprise air and/or ammonia. Ammonia can emerge from the urea/water solution, particularly at elevated temperatures. This process is also referred to as "outgassing". By way of example, deposits can consist of crystalline urea, which is precipitated out of the urea/water solution.

Once the reference surface has been cleaned after step b), there is a second measurement of a second propagation time of an ultrasonic signal to the reference surface, with the propagation time being determined on a straight path from the ultrasonic sensor to the reference surface and back to the ultrasonic sensor.

Subsequently the fill level is calculated in step d) from the first propagation time and the second propagation time. In this calculation, a propagation speed of the ultrasonic signal in the liquid additive is initially determined with the aid of the second propagation time and the known distance between the ultrasonic sensor and the reference surface. A distance between the liquid level and the ultrasonic sensor is established from the first propagation time with the aid of this propagation speed. The fill level in turn is calculated from this distance. It is also possible for the distance between the liquid level and the ultrasonic sensor to be used directly as value representative for the fill level. The calculation which is explained step-by-step here can be stored in the form of a calculation routine in a control instrument.

An ultrasonic pulse is a particularly effective and fast option for cleaning reference surfaces for an ultrasonic sensor. An ultrasonic pulse can be used to dissolve or remove both crystalline deposits and gas bubbles on the reference surfaces. The ultrasonic pulse energy is transmitted particularly well by the liquid additive and can thus be applied in a targeted manner on the reference surface in order to dissolve impurities on the reference surface. Ultrasonic pulses are particularly well suited for effective removal of ammonia gas bubbles which adhere to the reference surface. Such ammonia gas bubbles can arise as a result of partial conversion of the liquid additive in the tank.

Method step b) for cleaning the reference surface need not take place during each measurement with the aid of an ultrasonic signal. By way of example, it is possible for step b) only to be carried out at every tenth measurement. This can save energy required for the ultrasonic pulses. It may be the case that a preceding step d) possibly determines that the first propagation time does not reach the ultrasonic reception unit during a predetermined first propagation time interval and/or that the reflected/received response signal does not lie in a predetermined first response signal intensity range. If one of these two cases is determined, then step b) is carried out (immediately and/or during the next cycle of the described method). In this respect, it is possible to use step d) to check regularly whether cleaning of the reference surfaces is necessary and to carry out method step b) only if this is the case.

Moreover, method steps a) to d) are preferably repeated iteratively in the manner of a loop. The order of steps a) to d) is not fixed. The order can also be different. By way of example, the cleaning step b) could take place initially prior to both propagation time measurements (steps a) and c)).

The described method is particularly advantageous if the at least one ultrasonic pulse has a higher energy than the ultrasonic signals. The energy contained in the ultrasonic pulse preferably is at least five times and particularly preferably even at least twenty times the energy contained in the ultrasonic signal (used for the measurement).

In particular, the energy of an ultrasonic pulse or of an ultrasonic signal is dependent on the frequency, the amplitude and the duration of the ultrasonic pulse or of the ultrasonic signal. A high energy of the ultrasonic pulse brings about a particularly good and thorough cleaning of the reference surfaces. At the same time, the energy used for the ultrasonic signal can be reduced by regular cleaning with the aid of the ultrasonic pulse because a precise measurement of the propagation time is still possible, even in the case of a lower energy of the ultrasonic signals, if the reference surfaces are thoroughly cleaned on a regular basis.

Since a response signal to the ultrasonic pulse should not be monitored and because there is no propagation time measurement with the aid of the ultrasonic pulse, it is advantageous if the ultrasonic reception unit of the ultrasonic sensor is deactivated when the ultrasonic pulse is emitted. This can avoid damage to the ultrasonic reception unit by the ultrasonic pulse. By way of example, such damage could occur because the ultrasonic pulse is so strong that it cannot be processed by the reception unit.

The method is furthermore advantageous if the ultrasonic pulse is emitted by the same ultrasonic sensor as the ultrasonic signals.

Thus, the ultrasonic transmission unit in the ultrasonic sensor is preferably used to emit the ultrasonic pulse as well.

This embodiment variant of the described method renders it possible to carry out the method without additional components on the fill-level sensor. However, the ultrasonic transmission unit of the ultrasonic sensor then needs to have sufficient dimensions in order to emit a suitable ultrasonic pulse for cleaning the reference surfaces.

The method is furthermore advantageous if the ultrasonic pulse in step b) is produced by a separate ultrasonic cleaning instrument.

The ultrasonic cleaning instrument only requires an ultrasonic transmission unit for emitting the ultrasonic pulse.

There is no need for an ultrasonic reception unit because (as described further above) the ultrasonic pulse is not monitored any further.

This ultrasonic cleaning instrument can optionally also be provided in cumulative fashion, for example if different characteristics of step b) are carried out by the ultrasonic sensor and the ultrasonic cleaning instrument. By way of example, it is possible that light cleaning of the reference surface using an ultrasonic pulse from the ultrasonic sensor occurs regularly in step b) and that more thorough cleaning using an ultrasonic pulse of an ultrasonic cleaning instrument takes place in the case where significant dirtying of the reference surface is identified. By way of example, such significant dirtying can be identified using step d), which is already explained above.

Emitting the ultrasonic pulse using an ultrasonic cleaning instrument separate from the ultrasonic sensor is advantageous in that the ultrasonic cleaning instrument can be dimensioned and designed separately from the ultrasonic sensor in order to enable a particularly good and effective cleaning process. By way of example, it may be the case that the ultrasonic sensor cannot be used to produce a sufficiently strong ultrasonic pulse with which good cleaning of the reference surfaces is possible. It is also possible to arrange the ultrasonic cleaning instrument particularly advantageously for cleaning. By way of example, this can be brought about by virtue of arranging the ultrasonic cleaning instrument in the direct vicinity of the reference surfaces.

The method is furthermore advantageous if provision is made for at least two reference surfaces and at least one of the following parameters is determined in a step e) with the aid of different second propagation times to different reference surfaces:

a quality of the liquid additive; and
a concentration of urea in the liquid additive.

The propagation speed of ultrasonic signals in the liquid additive is at least partly dependent on the quality of the liquid additive or on the concentration of urea in the liquid additive in the case where the liquid additive is a urea/water solution. Using different propagation times to different reference surfaces in the tank, a measurement of quality and/or concentration can be made by comparing the different propagation times. This is a particularly effective option for connecting the fill-level measurement in the tank with the measurement of quality and concentration.

Different reference surfaces can also be provided in order to minimize or improve production tolerances. By way of example, it may be simpler to maintain precisely the distance between two reference surfaces than the distance between the ultrasonic sensor and a reference surface. This applies in particular if the ultrasonic sensor is arranged outside of the tank and not directly in the liquid additive. In this case, it is possible to disregard imprecision in respect of the distance between the ultrasonic sensor and the reference surface by comparing two propagation time measurements to two reference surfaces. It is therefore also possible for two propagation time measurements to two reference surfaces to be carried out in step c), and these two propagation time measurements can then be used in step d) for calculating the fill level.

The method is furthermore advantageous if at least two ultrasonic pulses are emitted in step b) for cleaning the at least one reference surface.

It is preferable for even more than three or, for example, for even more than ten ultrasonic pulses to be emitted for cleaning the reference surface. Here, impurities on the reference surface are dissolved further by each ultrasonic pulse. There can therefore be particularly effective and simple cleaning using a plurality of ultrasonic pulses, during which the energy input required for cleaning is possibly even lower than if use were made of only a single long ultrasonic pulse. The ultrasonic pulses can preferably follow one another in an impulsive fashion.

The method is furthermore advantageous if, after a reference surface has been cleaned, a test measurement is carried out in step b) using an ultrasonic signal from the ultrasonic sensor in order to check whether the cleaning was successful and another ultrasonic pulse is emitted for cleaning a reference surface if the cleaning was unsuccessful.

By way of example, the test measurement can be brought about by virtue of carrying out a propagation time measurement of an ultrasonic signal to the reference surface and subsequently carrying out a plausibility check for the result of this propagation time measurement. If the propagation time measurement yields a propagation time which lies in a plausible range, the assumption is made that the reference surface is completely cleaned. If the propagation time measurement yields an implausible propagation time, which, for example, deviates by more than 10 percent, more than 20 percent or even more than 50 percent from an expected propagation time or in which no (usable) response signal of a reflection of the ultrasonic signal at the reference surface is recorded, the assumption can be made that there has not yet been sufficient cleaning of the reference surface. In this case another ultrasonic pulse is emitted. It is also possible for the strength of the response signal to be evaluated in a test measurement in order to assess the cleaning. By way of example, if the response signal is weaker than the expected response signal by more than 10, more than 20 or even more than 50%, the assumption can be made that there has not yet been sufficient cleaning of the reference surface.

This procedure can be carried out so often until the test measurement yields that the reference surface has been cleaned sufficiently. However, it is also possible to set an upper threshold for the number of cycles, after which no further ultrasonic pulses are emitted for cleaning purposes. By way of example, the assumption can be made after more than five or more than ten test measurements that cleaning the reference surface with the aid of the ultrasonic sensor is not working. The process can then be aborted. Since the fill level of the liquid additive in the tank can no longer be sensibly monitored in this case either, an error signal can then be transmitted to a control instrument, said error signal being evaluated within the scope of an onboard diagnosis.

It is furthermore advantageous if the ultrasonic pulse has a frequency between 20 kHz [kilohertz] and 2 MHz [megahertz]. The frequency of the ultrasonic pulse preferably lies between 20 kHz and 40 kHz. Particularly effective cleaning is possible using such an ultrasonic pulse.

The method is also advantageous if an ultrasonic pulse has a duration of between 10 milliseconds and 20 seconds. The assumption can be made for these lengths of ultrasonic pulses that sufficient cleaning of the reference surface is obtained.

It is furthermore advantageous if pressure peaks of at least 100 bar occur at the at least one reference surface as a result of an ultrasonic pulse. The pressure peaks are preferably even greater than 1000 bar or even greater than 10 000 bar. Such high pressures during the pressure peaks can for example be obtained as a result of a suitable selection of frequency and amplitude of the ultrasonic pulse.

These pressure peaks occur while the ultrasonic waves impact on the reference surface. These pressure peaks have a very short duration. The duration of the pressure peaks is dependent on the frequency of the ultrasonic waves of the ultrasonic pulse. One (separate) pressure peak typically occurs during one oscillation. By way of example, in the case of a frequency of 20 kHz a pressure peak is shorter than 0.05 milliseconds. The pressure peaks arise from the high-frequency longitudinal movement (in the propagation direction of the ultrasonic pulse) of the liquid additive during the ultrasonic pulse. Although the pressure peaks are so short, the pressure peaks are able to dissolve even very solid deposits or very securely adhering bubbles on the reference surfaces. The pressure peaks generate a significant force on the deposits or the bubbles.

Furthermore, a delivery unit for installation in a tank for a liquid additive is specified, having at least one ultrasonic sensor and an electronics module, wherein the described method can be carried out by means of the delivery unit. In other words, this means, in particular, that the delivery apparatus is suited to and configured for carrying out the method.

The delivery unit preferably has a housing which can be inserted into an opening in the bottom of the tank. The delivery unit seals this opening in the tank bottom in a fluid-tight fashion. The ultrasonic sensor is arranged in the housing of the delivery unit and, in the state where it is installed in the tank, aligned such that it is aligned towards a liquid level in the tank. The delivery unit furthermore has a suction point, at which liquid additive can be removed from the tank. Moreover, the delivery unit has a line connector, to which a line can be connected through which the liquid additive can be conducted away from the delivery unit. A pump for delivering the liquid additive is preferably also provided in the delivery unit. The electronics module in the delivery unit is preferably connected directly to the ultrasonic sensor and controls or monitors the measuring of the fill level by means of the ultrasonic sensor. The electronics module can also be configured to carry out the cleaning of the reference surface as per the described method. The electronics module can also have a control unit, by means of which at least one ultrasonic sensor is operated, wherein provision can also be made for an evaluation unit for capturing and evaluating the response signals.

Moreover, a motor vehicle is proposed, which has a combustion engine and an exhaust-gas treatment device for purifying the exhaust gases of the combustion engine, said exhaust-gas treatment device having an SCR catalytic converter by means of which the method of selective catalytic reduction can be carried out. Liquid additive can fed to the exhaust-gas treatment device via an addition device.

The liquid additive is delivered to the addition device from a tank along a supply line by means of an above-described delivery unit. The motor vehicle preferably has a control instrument which monitors the supply with the addition device and the delivery with the delivery unit. This control instrument can also be configured to initiate or monitor the carrying out of the described method. Here, the control instrument can have a control unit by means of which at least one ultrasonic sensor is operated, wherein provision can also be made for an evaluation unit for capturing and evaluating the response signals.

BRIEF DESCRIPTION OF THE SEVERAL VIEWS OF THE DRAWING

The invention and the technical field will be explained in more detail below on the basis of the figures. The figures show particularly preferred exemplary embodiments; however, the invention is not restricted to these. In particular, reference is to be made to the fact that the figures and the illustrated proportions are only of a schematic nature. In detail.

DESCRIPTION OF THE INVENTION

Figure 1:
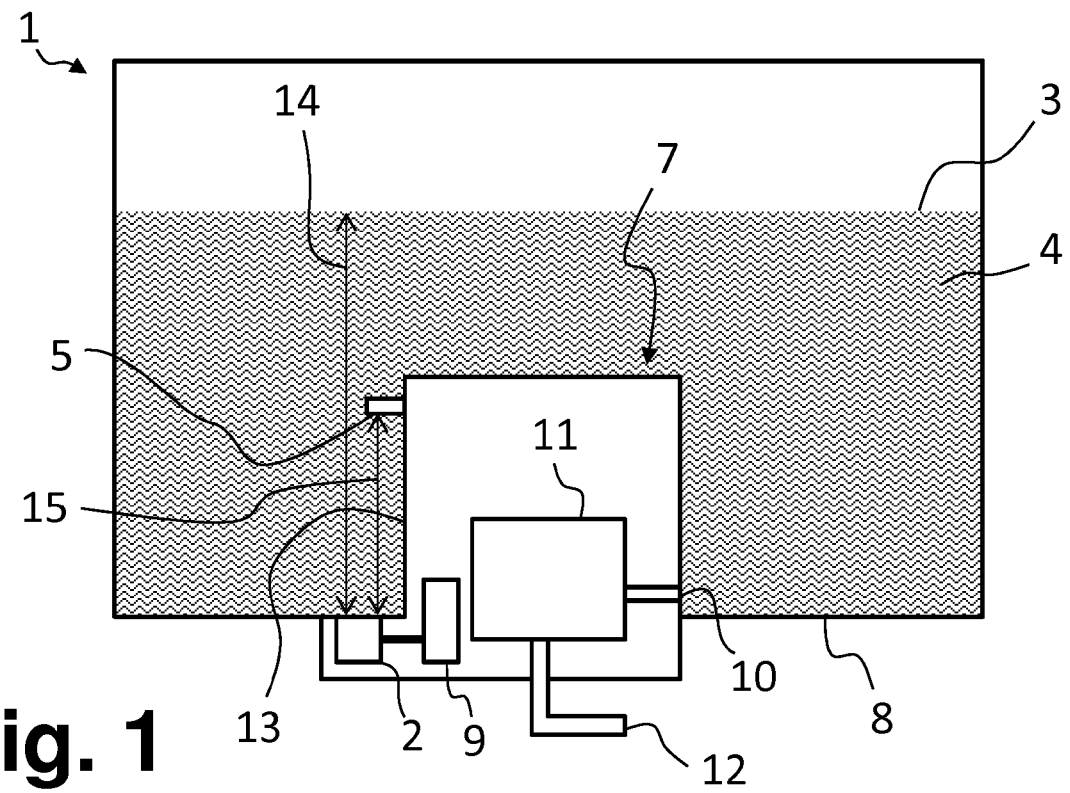
FIG. 1: shows a first embodiment variant of a delivery unit for the described method.
Figure 2:
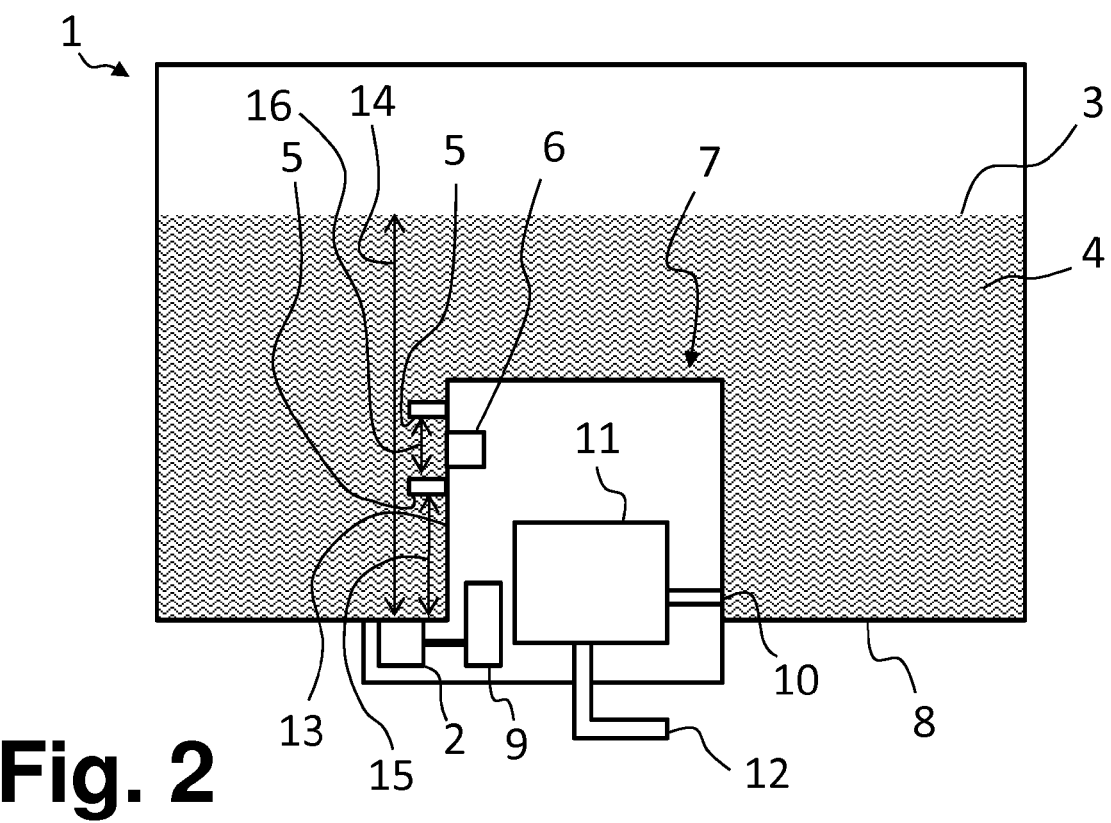
FIG. 2: shows a second embodiment variant of a delivery unit for the described method.

FIGS. 1 and 2 illustrate two different embodiment variants of delivery units 7 for the described method, which will initially be explained together here. Both delivery units 7 have a housing 13 and are installed in a tank bottom 8 of a tank 1 in which liquid additive 4 is stored. A liquid level 3 of the liquid additive 4 arises in the tank 1 due to gravity. The liquid additive 4 is present below the liquid level 3. There is gas, or air in particular, above the liquid level 3. The delivery unit 7 removes liquid additive 4 from the tank 1 at a suction point 10 and delivers it, using a pump 11, to a line connector 12, at which a line to an addition device can be connected. The delivery units 7 respectively have one ultrasonic sensor 2, which may be connected to an electronics module 9. The ultrasonic sensor 2 is configured to emit an ultrasonic signal along a first path 14 to the liquid level 3. The ultrasonic signal is then reflected at the liquid level 3 and propagates back to the ultrasonic sensor 2 along the first path 14. The ultrasonic sensor 2 is also configured to emit an ultrasonic signal along the second path 15 to a reference surface 5. The ultrasonic signal is also reflected at the reference surface 5 and it then propagates back to the ultrasonic sensor 2.

In the embodiment variant as per FIG. 1, the ultrasonic pulse is likewise produced by the ultrasonic sensor 2. Thus, the ultrasonic sensor 2 cleans the reference surface 5 by means of at least one ultrasonic pulse.

In the embodiment variant as per FIG. 2, provision is made for an additional ultrasonic cleaning instrument 6, by means of which ultrasonic pulses are emitted for cleaning the reference surfaces 5.

In the embodiment variant as per FIG. 2, provision is moreover made for two reference surfaces 5, between which a third path 16 exists. This third path 16 can be used to measure the speed of an ultrasonic signal in the liquid additive 4 independently of the length of the second path 15. This renders it possible to reduce production tolerances in respect of the position of the ultrasonic sensor. Moreover, the different propagation time measurements can also be used to determine the quality and/or the concentration of the liquid additive 4.

Figure 3:
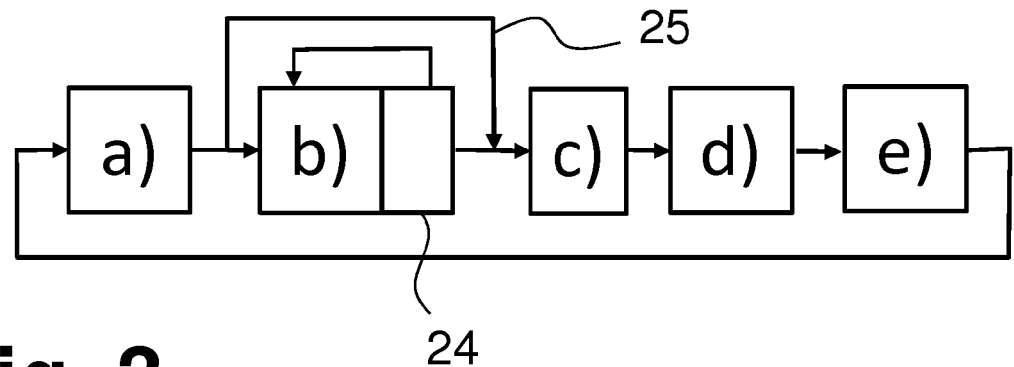
FIG. 3: shows a flowchart of the described method.

FIG. 3 shows a flowchart of the described method. Method steps a), b), c) and d), as well as the optional method step e) for measuring a quality or a concentration of the liquid additive can be identified. It is likewise indicated that the method is repeated iteratively according to a loop. It is possible to identify that a test step 24 can adjoin step b), which can also still be counted as part of method step b). If the test in the test step 24 yields that the reference surfaces have not yet been cleaned, method step b) can be repeated. It is also possible to identify the bypass 25, according to which method step b) can be bypassed. In order to save energy it is not necessary for method step b) to be carried out during each iteration of the described method.

Figure 4:
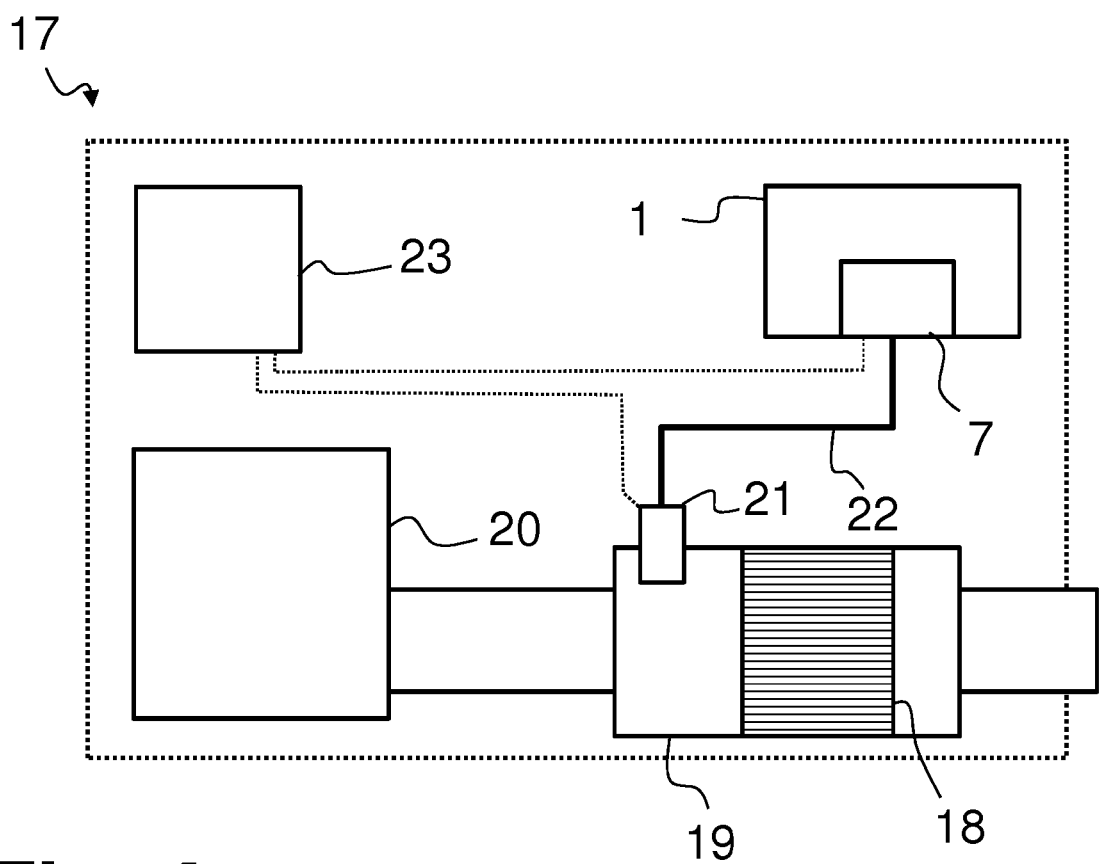
FIG. 4: shows a motor vehicle, having a delivery unit for the described method.

FIG. 4 shows a motor vehicle 17, having a combustion engine 20 and an exhaust-gas treatment device 19 with an SCR catalytic convertor 18 for purifying the exhaust gases of the combustion engine 20. A liquid additive can be fed to the exhaust-gas treatment device 19 by means of an addition device 21. The addition device 21 is supplied with liquid additive from the tank 1 via a supply line 22 by a delivery unit 7. The motor vehicle 17 additionally has a control instrument 23, by means of which the operation of the addition device 21 and the operation of the delivery unit 7 can be monitored and which can also be configured to initiate or carry out the described method.

By way of precaution, reference is made to the fact that the combinations of features in the figures are not mandatory (provided that reference was not explicitly made here thereto), but rather that subcomponents of one figure can also be combined with subcomponents of other figures. This applies, in particular, in respect of the number, the location, the alignment, the type of the ultrasonic sensors and/or of the ultrasonic cleaning instruments and/or of the reference surfaces.

The method described here enables particularly effective cleaning of reference surfaces for an ultrasonic sensor in a tank for liquid additive and, as a result, enables particularly precise measurements of the fill level of the liquid additive in a tank with the aid of an ultrasonic sensor.

LIST OF REFERENCE SIGNS

1 Tank
2 Ultrasonic sensor
3 Liquid level
4 Liquid additive
5 Reference surface
6 Ultrasonic cleaning instrument
7 Delivery unit
8 Tank bottom
9 Electronics module
10 Suction point
11 Pump
12 Line connector
13 Housing
14 First path
15 Second path
16 Third path
17 Motor vehicle
18 SCR catalytic convertor
19 Exhaust-gas treatment device
20 Combustion engine
21 Addition device
22 Supply line
23 Control instrument
23 Test step
25 Bypass

The invention claimed is:

1. A method for measuring a fill level of a liquid additive in a tank using an ultrasonic sensor, the method comprising the following steps:
   a) measuring a first propagation time of an ultrasonic signal from the ultrasonic sensor to a liquid level of the liquid additive;
   b) cleaning at least one reference surface in the liquid additive by using at least one ultrasonic pulse;
   c) measuring at least one second propagation time of an ultrasonic signal from the ultrasonic sensor to the at least one reference surface; and
   d) calculating the fill level from the first propagation time and the second propagation time.

2. The method according to claim 1, which further comprises providing the at least one ultrasonic pulse with a higher energy than the ultrasonic signals.

3. The method according to claim 1, which further comprises emitting the at least one ultrasonic pulse from the same ultrasonic sensor as the ultrasonic signals.

4. The method according to claim 1, which further comprises producing the at least one ultrasonic pulse in step b) by using a separate ultrasonic cleaning instrument.

5. The method according to claim 1, which further comprises:
   providing at least two reference surfaces; and
   determining at least one of the following parameters in a step e) by using different second propagation times to different reference surfaces:
   a quality of the liquid additive, and
   a concentration of urea in the liquid additive.

6. The method according to claim 1, which further comprises emitting at least two ultrasonic pulses in step b) for cleaning the at least one reference surface.

7. The method according to claim 1, which further comprises providing the at least one ultrasonic pulse with a frequency between 20 kilohertz and 2 megahertz.

8. The method according to claim 1, which further comprises providing the at least one ultrasonic pulse with a duration of between 10 milliseconds and 20 seconds.

9. The method according to claim 1, which further comprises causing pressure peaks of at least 100 bar to occur at the at least one reference surface as a result of the at least one ultrasonic pulse.

10. A method for measuring a fill level of a liquid additive in a tank using an ultrasonic sensor, the method comprising the following steps:
    a) measuring a first propagation time of an ultrasonic signal from the ultrasonic sensor to a liquid level of the liquid additive;
    b) cleaning at least one reference surface in the liquid additive by using at least one ultrasonic pulse;
    c) measuring at least one second propagation time of an ultrasonic signal from the ultrasonic sensor to the at least one reference surface; and
    d) calculating the fill level from the first propagation time and the second propagation time;
    after the at least one reference surface has been cleaned:
       carrying out a test measurement in step b) using an ultrasonic signal from the ultrasonic sensor in order to check if the cleaning was successful, and
       emitting another ultrasonic pulse for cleaning the at least one reference surface if the cleaning was unsuccessful.

11. A delivery unit for installation in a tank for a liquid additive, the delivery unit comprising:
    at least one reference surface in the liquid additive;
    at least one ultrasonic sensor; and
    an electronics module for measuring a fill level of the liquid additive in the tank by using said at least one ultrasonic sensor, said electronics module being programmed to carry out the following steps:
    a) measuring a first propagation time of an ultrasonic signal from said at least one ultrasonic sensor to a liquid level of the liquid additive;
    b) cleaning said at least one reference surface by using at least one ultrasonic pulse;
    c) measuring at least one second propagation time of an ultrasonic signal from said at least one ultrasonic sensor to said at least one reference surface; and d) calculating the fill level from the first propagation time and the second propagation time.

\* \* \* \* \*